United States Patent [19]

Takeuchi

[11] Patent Number: 5,379,102

[45] Date of Patent: Jan. 3, 1995

[54] SYSTEM FOR IDENTIFYING JEWELS

[75] Inventor: Masaaki Takeuchi, Nagoya, Japan

[73] Assignee: E.R.C. Company Ltd., Nagoya, Japan

[21] Appl. No.: 995,078

[22] Filed: Dec. 22, 1992

[30] Foreign Application Priority Data

Dec. 24, 1991 [JP] Japan ................................. 3-357016

[51] Int. Cl.⁶ ............................................. G01N 21/87
[52] U.S. Cl. .......................................... 356/30; 356/72
[58] Field of Search ................. 356/319, 445, 448, 30, 356/72

[56] References Cited

FOREIGN PATENT DOCUMENTS 57-153244  9/1982  Japan .
57-156545  9/1982  Japan .
57-159358  10/1982 Japan .
57-165742  10/1982 Japan .
57-171249  10/1982 Japan .
58-15102   1/1983  Japan .
59-125045  7/1984  Japan .

Primary Examiner—F. L. Evans
Assistant Examiner—Peter J. Rashid

[57] ABSTRACT

A system for identifying jewels comprises an automatic microscope 2, an automatic image-analyzing apparatus 3, an electric-resistance measuring apparatus 4, a weighing apparatus 5, a spectroscopic-analysis apparatus 6, and an electronic information processing apparatus 7. The microscope 2 forms an enlarged image of an identification number 11d marked on a jewel to be identified. The image-analyzing apparatus 3 receives the image of the identification number 11d from the microscope 2, and analyzes it. The measuring apparatus 4 measures the electric resistance between spots 11a and 11b marked on the jewel. The weighing apparatus 5 determines the specific gravity of the jewel to the nearest 0.001 gram. The spectroscopic-analysis apparatus 6 directs a beam of light of particular band on a spot 11c marked on the jewel, and determines the spectrum of the light reflected from the spot 11c. Electric signals to represent the results of measurements conducted in the apparatuses 3, 4, 5, and 6 are output to the processing apparatus 7, which processes these signals and store them in memory.

1 Claim, 3 Drawing Sheets

SYSTEM FOR IDENTIFYING JEWELS

FIELD OF THE INVENTION

This invention relates to a system for identifying jewels.

BACKGROUND OF THE INVENTION

So far in most cases a jewel has been identified by determining its specific gravity, determining its index of refraction, determining whether it refracts a light ray in a single direction or two directions, or examining it with a spectroscope. These identifying methods, however, may require a great deal of skill or may not be always completely reliable.

SUMMARY OF THE INVENTION

Accordingly, it is the object of the invention to provide a jewel-identifying system which enables even a layman to identify a jewel with strict accuracy.

The system of the invention comprises an optical instrument, an automatic image-analyzing apparatus, an electric-resistance measuring apparatus, a weighing apparatus, a spectroscopic-analysis apparatus, and an electronic information processing apparatus. The optical instrument forms an enlarged image of an identification number marked on a jewel to be identified. The image-analyzing apparatus receives the image of the identification number from the optical instrument, and analyzes it. The electric-resistance measuring apparatus measures the electric resistance between first and second spots marked on the jewel. The weighing apparatus determines the specific gravity of the jewel to the nearest 0.001 gram. The spectroscopic analysis apparatus directs a beam of light of particular band on a third spot marked on the jewel, and determines the spectrum of the light reflected from the third spot. The image-analyzing apparatus generates an electric signal of the image of the identification number, and sends it to the information processing apparatus. In addition, electric signals to represent the results of measurements conducted in the electric-resistance apparatus, the weighing apparatus, and the spectroscopic-analysis apparatus are output to the information processing apparatus, which processes these signals and store them in memory.

BRIEF DESCRIPTION OF THE DRAWING

FIG. 3 shows a finger ring comprising a ring proper 10b and a gem 10a; and

DETAILED DESCRIPTION OF PREFERRED EMBODIMENT

Figure 1:
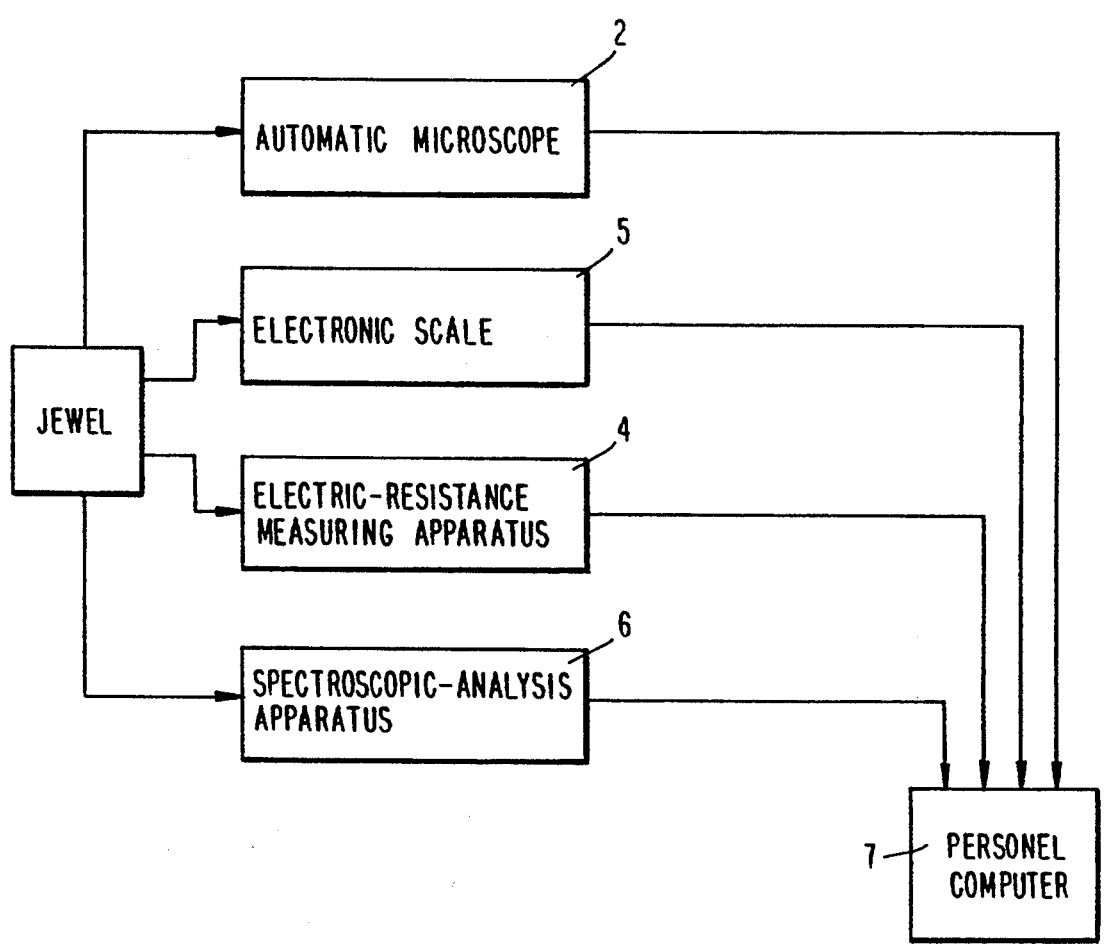
FIGS. 1 and 2 are schematic diagrams showing the construction of a jewel-identifying system of the invention.

A jewel-identifying system which embodies the invention in one preferred form will now be described in detail.

The system of the invention comprises an automatic microscope 2, an automatic image analyzing apparatus 3, an electric-resistance measuring apparatus 4, an electronic scale 5, a spectroscopic-analysis apparatus 6, and a personal computer 7.

Figure 3:
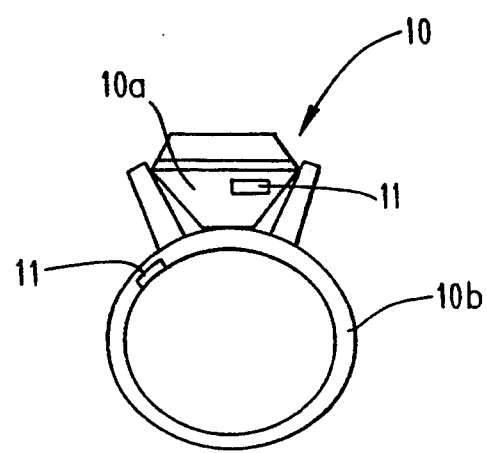
Figure 4:
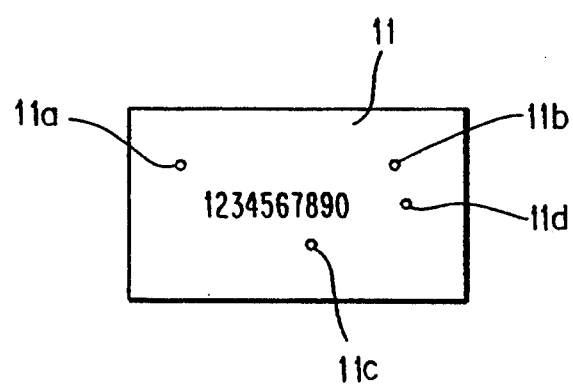
FIG. 4 shows an identifying area.

According to the invention, for a jewel to be identified, it is necessary to form on the jewel, in advance, at least one identifying area including an identification mark 11d, two spots, or dots, 11a and 11b for measuring electric resistance, and one spot 11c for spectroscopic analysis. FIG. 4 shows such an identifying area 11. As shown in FIG. 4, the identification mark 11d may be a given number. FIG. 3 shows a finger ring with two identifying areas 11. That is, one is formed on a gem 10a, and the other is formed on the ring proper, or metal portion, 10b.

For example, photo-etching may be employed to form an identifying area 11 on a jewel.

Figure 2:
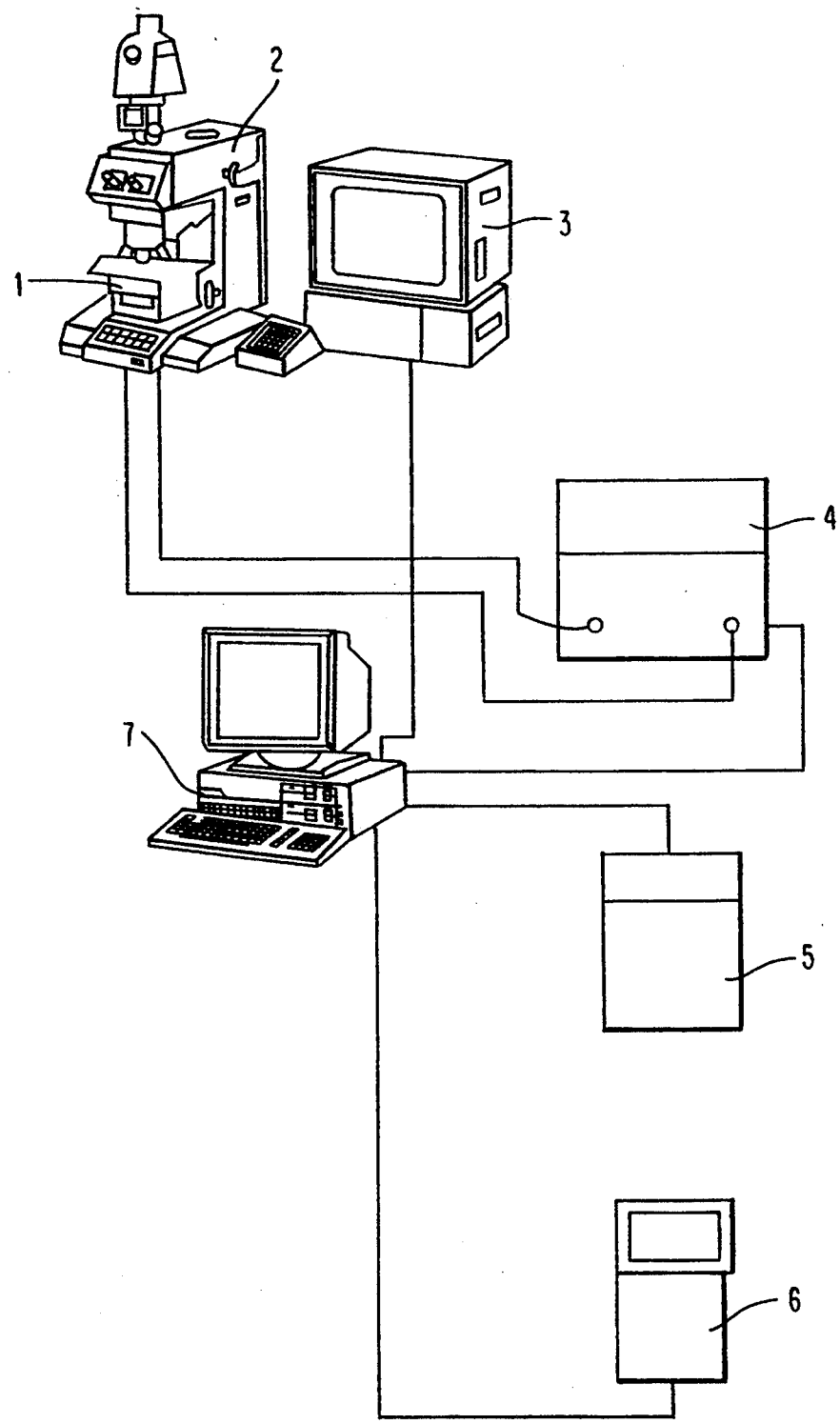

Referring to FIG. 2, a jewel to be identified is placed on a jewel support 1, and the automatic microscope 2 forms an enlarged view of the identifying area 11 of the jewel. The microscope 2 has substantially the same fundamental construction as a usual microscope, except that in the microscope 2 adjustment of the focus of the lens, movement of the object viewed, and change of the lens are all made automatically by a computer. The microscope 2 sends a signal of the image of the identification number 11d to the automatic image-analyzing apparatus 3.

The analyzing apparatus 3 is programed to analyze the foregoing signal. So the signal is analyzed thereby. Then, the analyzing apparatus 3 generates an electric signal (digital signal) of the image of the identification number 11d, and sends the electric signal to the personal computer 7.

The electric-resistance measuring apparatus 4 causes a very weak electric current to flow between the two spots 11a and 11b of the identifying area 11, and measures the electric resistance between the two spots. The electric resistance of an object depends partly on the nature of the material of which it is made. Thus, not only diamond and zirconium, for example, differ materially in electric resistance, but also two diamonds with identical shape differ, though slightly, in electric resistance if their inclusions are not identical. Therefore, measuring the electric resistance between the spots 11a and 11b makes it possible to distinguish not only between jewels of different materials but also between even jewels of the same material and same shape.

The electronic scale 5 determines the specific gravity of the jewel by measuring its weight in air and its weight in water. The scale 5 determines it to the nearest 0.001 gram.

The spectroscopic-analysis apparatus 6 directs a light of particular band on the spot 11c of the identifying area 11, and determines the spectrum of the light reflected from the spot 11c, and generates an electric signal (digital signal) to represent the pattern of the spectrum, and sends the electric signal to the personal computer 7.

The personal computer 7 may be a commercially available one. In use, it is necessary either to install in a hard disk a program for performing the identifying operation of the invention or to use a floppy disk containing the program. Personal computer 7 produces a database from the electric signals received from image analyzing apparatus 3, electric-resistance measuring apparatus 4, electronic scale 5, and spectroscopic-analysis apparatus 6. Also, personal computer 7 displays, on its screen, values stored in its memory, as well as relevant drawings, diagrams, graphs, and the like.

As described before, according to the invention, for a jewel to be identified, it is necessary to form on the jewel, in advance, at least one identifying area 11 including an identification mark 11d and three spots 11a, 11b, and 11c. A person who has rented a jewel from, for example, a jewel rental service may intentionally substitute an imitation for the entire jewel that she or he has rented. It will be appreciated that one identifying area 11 is sufficient to discover such a "crime." In contrast, FIG. 3 shows a finger ring with two identifying areas 11. That is, one is formed on a gem 10a, and the other is formed on the ring proper, or metal portion, 10b. Thus, if a person who has rented the ring of FIG. 3 intentionally separates either the gem 10a or the ring proper 10b from the rest and instead connects an imitation, this "crime" can be discovered without fail according to the invention. However, if an identifying area 11 is formed only on, for example, the gem 10a, it may be difficult to discover the crime of substituting an imitation for only the ring proper 10b. Therefore, as far as the jewel of FIG. 3 is concerned, two identifying areas are preferable to one.

After forming identifying area or areas 11 on the jewel, one then has to store necessary information of the jewel (as briefly described above) in the computer 7, as follows:

(1) Storing identification number

The jewel is placed on the jewel support 1. Then, the automatic microscope 2 is switched on. Thereupon, using supersonic waves, the microscope 2 determines the distance between the lens and the identifying number 11d of the jewel, and automatically adjusts the focus of the lens. Also, the microscope 2 selects the lens of suitable size for the size of the identifying area 11 of the jewel. The microscope 2 forms an enlarged view of the identifying area 11. A TV camera connected to the eyeglass of the microscope 2 takes a picture of the identification number 11d. A signal of this picture is output to the image analyzing apparatus 3. Thereupon the analyzing apparatus 3 analyzes the signal, and generates a digital signal of the image of the identification number 11d, and outputs the digital signal to the personal computer 7. When the computer 7 has received the signal, the computer 7 produces a file for that particular identification number 11d in a hard disk or in a floppy disk. For the sake of discussion, this file will be hereinafter referred to as a "first file."

(2) Storing electric resistance

Then, the jewel is removed from the jewel support 1, and is mounted in the electric-resistance measuring apparatus 4. Thereupon, the measuring apparatus 4 connects electric terminals to the respective spots 11a and 11b, and measures the electric resistance between the spots 11a and 11b, and outputs this information (electric resistance) to the computer 7. Thereupon the computer 7 stores this information in the first file.

(3) Storing specific gravity

Then, the jewel is removed from the measuring apparatus 4, and is mounted in the electronic scale 5. Thereupon, the scale 5 determines the specific gravity of the jewel, and outputs this information (specific gravity) to the computer 7. Thereupon the computer 7 stores this information in the first file.

(4) Storing pattern of spectrum

Then, the jewel is removed from the scale 5, and is mounted in the spectroscopic-analysis apparatus 6. Thereupon, as described before, the apparatus 6 directs a light of particular band on the spot 11c of the identifying area 11, and determines the spectrum of the light reflected from the spot 11c, and generates an electric signal (digital signal) to represent the pattern of the spectrum, and outputs this electric signal to the computer 7. Thereupon the computer 7 stores this information (pattern of spectrum) in the first file.

Four categories of information for identifying the particular Jewel are stored in the computer in this manner. That is, this particular jewel is registered in the first file. Thus this particular Jewel is now ready to be identified.

Various jewels can be registered in the computer 7 in the same manner.

To determine whether a jewel is the identical one registered in a particular file, the operator first operates the keyboard of the computer 7 to command the computer 7 to compare the four pieces of information in that file and new four pieces of information which will now be supplied to the computer 7. Then, for the jewel to be examined, the operator conducts the same measurements as in (1) to (4) above. The results of measurements, or new four pieces of information, are sent to the computer 7. Thereupon, the computer 7 compares the information. Then, if all information coincide, the computer 7 identifies the jewel examined as being the one registered in the file. If the pieces of information of even a single category do not coincide with each other, the computer 7 determines that the jewel examined is not the one registered in the file. The result is displayed on the screen of the computer 7, together with all pieces of information compared.

When necessary, the operator can make the computer display the information of any desired jewel (registered in the computer) on the screen only by entering the identification number 11d of that jewel from the keyboard.

What is claimed is:

1. A system for identifying a jewel having a gem (10a) and a metal portion (10b), each of which is marked with an identification number (11d) and a first spot (11a), a second spot (11b) and a third spot (11c), said system comprising (a) an identification-number reading apparatus for reading the identification number (11d), (b) an electric-resistance measuring apparatus (4) for measuring an electric resistance between each first spot (11a) and each second spot (11b) and for generating an electric signal to represent the electric resistance, (c) a specific-gravity measuring apparatus (5) for measuring the specific gravity of the jewel by determining its weight in air and its weight in water and generates an electric signal representing the specific gravity, (d) a spectroscopic-analysis apparatus (6) for directing a beam of light of selected band width on said third spot (11c) to determine the spectrum of the light reflected from the third spot (11c) and for generating an electric signal to represent a pattern of said spectrum, and (e) an electric information processing apparatus (7) for receiving and processing said electric signals and for storing them in memory, wherein (i) said reading apparatus includes an automatic microscope (2) for reading the identification number (11d) and generating a signal of the image of the identification number (11d) and an apparatus (3) for receiving the signal from the automatic microscope (2) and analyzing and processing the same, (ii) said electric-resistance measuring apparatus (4) includes means for causing a weak current to flow between said first and second spots (11a), (11b), and (iii) said specific gravity measuring apparatus (5) comprising an electronic scale which measures the weight of the jewel in air and its weight in water to the nearest 0.001 gram.

* * * * *